(12) United States Patent
Galavis et al.

(10) Patent No.: US 9,355,447 B2
(45) Date of Patent: May 31, 2016

(54) SYSTEM AND METHOD FOR GRADIENT ASSISTED NON-CONNECTED AUTOMATIC REGION (GANAR) ANALYSIS

(71) Applicant: Wisconsin Alumni Research Foundation, Madison, WI (US)

(72) Inventors: Paulina E. Galavis, Madison, WI (US); Bhudatt Paliwal, Madison, WI (US); James Holden, Madison, WI (US); Robert Jeraj, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 171 days.

(21) Appl. No.: 13/971,913

(22) Filed: Aug. 21, 2013

(65) Prior Publication Data

US 2015/0055849 A1 Feb. 26, 2015

(51) Int. Cl.
| | | |
|---|---|---|
| G06K 9/00 | (2006.01) | |
| G06T 7/00 | (2006.01) | |
| G06T 7/40 | (2006.01) | |
| A61N 5/10 | (2006.01) | |

(52) U.S. Cl.
CPC .............. *G06T 7/0012* (2013.01); *G06T 7/0081* (2013.01); *G06T 7/0091* (2013.01); *G06T 7/401* (2013.01); *A61N 5/103* (2013.01); *G06T 2207/10104* (2013.01); *G06T 2207/10108* (2013.01); *G06T 2207/20144* (2013.01); *G06T 2207/30016* (2013.01); *G06T 2207/30096* (2013.01)

(58) Field of Classification Search
CPC ....... G06T 7/0012; G06T 7/0081; A61N 5/00
See application file for complete search history.

(56) References Cited

U.S. PATENT DOCUMENTS

| | | | | |
|---|---|---|---|---|
| 7,636,420 | B2* | 12/2009 | Spies et al. ................... | 378/65 |
| 7,783,094 | B2* | 8/2010 | Collins et al. ................. | 382/128 |
| 7,995,813 | B2* | 8/2011 | Foshee et al. ................. | 382/128 |
| 8,577,107 | B2* | 11/2013 | Hibbard ................... | G06T 17/30 |
| | | | | 128/922 |
| 8,788,020 | B2* | 7/2014 | Mostafavi et al. ............. | 600/428 |
| 2005/0251029 | A1* | 11/2005 | Khamene ............. | A61B 8/4245 |
| | | | | 600/427 |
| 2007/0211939 | A1* | 9/2007 | Kaus ........................ | A61B 6/00 |
| | | | | 382/173 |
| 2009/0187422 | A1* | 7/2009 | Kaus ....................... | A61B 6/466 |
| | | | | 705/2 |
| 2009/0226065 | A1* | 9/2009 | Chen ................. | G06F 17/30262 |
| | | | | 382/131 |
| 2010/0114597 | A1* | 5/2010 | Shreiber ............... | G06F 19/321 |
| | | | | 705/2 |
| 2011/0282193 | A1* | 11/2011 | Amberg et al. ............... | 600/431 |

(Continued)

OTHER PUBLICATIONS

Simon K. Warfield et al, Simultaneous Truth and Performance Level Estimation (STAPLE): An Algorithm for the Validation of Image Segmentation, Jul. 2004, IEEE Transaction on Medical Imaging, vol. 23, No. 7, pp. 903-921.*

(Continued)

*Primary Examiner* — Gregory M Desire
(74) *Attorney, Agent, or Firm* — Quarles & Brady, LLP (57) ABSTRACT

A system and method for analyzing medical images of a subject includes acquiring the medical images of the subject and texture images. A computer system determines, using the medical images and the texture feature images, a plurality of segmentation surfaces by iteratively adjusting a relationship between a region growing algorithm that selects a region of interest (ROI) to determine a given segmentation surface and cost function for evaluating the given segmentation surface. The computer system generates a report using the plurality of segmentation surfaces indicating at least boundaries between anatomical structures with functional differences in the medical images.

20 Claims, 6 Drawing Sheets

(56) References Cited

U.S. PATENT DOCUMENTS

| | | | | |
|---|---|---|---|---|
| 2012/0136677 | A1* | 5/2012 | Ziegenhein | A61N 5/1031 705/2 |
| 2013/0077752 | A1* | 3/2013 | Zankowski | A61N 5/1031 378/65 |
| 2013/0267755 | A1* | 10/2013 | Chebrolu et al. | 600/1 |
| 2013/0272593 | A1* | 10/2013 | Lee et al. | 382/131 |
| 2015/0055849 | A1* | 2/2015 | Galavis et al. | 382/132 |

OTHER PUBLICATIONS

Galavis, et al., Abstract ID: 13275. Title: Impact of Image Acquisition Mode and Reconstruction Parameters on Target Volume Definition Using PET-Thresholded-Based Segmentation, AAPM Annual Meeting, 2010, Philadelphia, 2 pages.

Galavis, et al., Comparative Study of Tumor Volume Segmentation Techniques and Their Sensitivity to PET Imaging Parameters, Joint AAPM/COMP Meeting, 2011, Vancouver, 4 pages.

Geets, et al., A Gradient-Based Method for Segmenting FDG-PET Images: Methodology and Validation, Eur. J. Nucl. Med. Mol. Imaging, 2007, 34:1427-1438.

Mumford, et al., Optimal Approximations by Piecewise Smooth Functions and Associated Variational Problems, Communications on Pure and Applied Mathematics, 1989, 42(5):577-685.

Otsu, A Threshold Selection Method from Gray-Level Histograms, IEEE Transactions on Systems, Man and Cybernetics, 1979, SMC-9(1):62-66.

Revol, et al., A New Minimum Variance Region Growing Algorithm for Image Segmentation, Pattern Recognition Letters, 1997, 18:249-258.

Tang, Texture Information in Run-Length Matrices, IEEE Transactions on Image Processing, 1998, 7(11):1602-1609.

Warfield, et al., Simultaneous Truth and Performance Level Estimation (STAPLE): An Algorithm for the Validation of Image Segmentation, IEEE Transactions on Medical Imaging, 2004, 23(7):903-921.

\* cited by examiner

SYSTEM AND METHOD FOR GRADIENT ASSISTED NON-CONNECTED AUTOMATIC REGION (GANAR) ANALYSIS

STATEMENT REGARDING FEDERALLY SPONSORED RESEARCH

This invention was made with government support under CA136927 awarded by the National Institutes of Health. The government has certain rights in the invention.

CROSS-REFERENCE TO RELATED APPLICATIONS

N/A

BACKGROUND OF THE INVENTION

The field of the invention is image analysis and processing. More particularly, the invention relates to systems and methods for processing and segmenting images, for example, for use in therapy planning, such as for radiation therapy.

Many modern medical treatments rely heavily on planning procedures that utilize medical images to facilitate the planning. For example, modern radiation therapy procedures are preceded by substantial planning processes that dictate how the radiation therapy will be performed. As another example, robotically-driven surgical procedures, include radiosurgery procedures, rely on extensive planning. Not surprisingly, the effectiveness of any particular planning procedure is necessarily limited by the detail and accuracy of the underlying information used for planning.

In treatment planning procedures, medical images provide the fundamental basis of information upon which planning is conducted. Traditionally, many planning procedures have relied upon anatomical images, such as are readily provided by computed tomography (CT) or magnetic resonance (MR) imaging systems. These and other modalities provide exceptional anatomical information, but often struggle to impart any physiological information.

More recently, imaging modalities, such as positron emission tomography (PET), have become a prevalent resource in medical planning because PET images (and other such imaging modalities, such as single photon emission tomography (SPECT) and the like) provide extensive physiological and/or biological information that is unavailable from imaging modalities such as CT and MR systems. For example, PET, in particular, has become a common tool used for radiotherapy target definition and for treatment assessment. PET images provide functional information that can be incorporated into the localization and planning process to further improve tumor delineation, especially when tumors are difficult to define from anatomical images, such as provided by CT systems, or when the tumor boundaries are not easily distinguished from the normal surrounding tissue. Another reason for integrating PET in the gross tumor volume (GTV) definition is its higher sensitivity and specificity for malignant disease. Therefore, a reliable and robust segmentation method is of utmost importance, given that under-dosing a tumor may lead to recurrence while over-dosing of the normal surrounding tissue could lead to severe side effects to the patients. Unfortunately, PET images provide poor anatomical detail and, as a result of this limitation and others, segmentation can be difficult.

Multiple approaches for segmentation have been proposed in the literature, but the most prevalent approach for auto-segmentation of PET target volumes is threshold segmentation, based on fixed uptake values or local contrast. More sophisticated auto-segmentation approaches include gradient-based, region-growing, texture-feature, and statistical-based segmentation methods. All of these methods have additional drawbacks associated with necessary parameter determination during the pre-processing steps. For example, in the case of the gradient-based approach, a pre-processing step using a bilateral filter is required to smooth the image. In the case of feature-based methods, a training data set is required and serves as a limiting factor in the accuracy. In the statistical approach, initial class estimates are required. The need of pre-processing steps or additional information make the use of these algorithms more complicated and the outcome dependent on choices made by the user. Particularly in light of the requirement of user input, these methods can have substantial variability.

In addition, PET images are affected by inherent uncertainties, such as physical, biological, and technical factors. The physical factors include acquisition mode and image reconstruction parameters. Biological factors refer to glucose level in the blood, uptake periods, and motion, among others. The technical factors include, but are not limited to, residual activity in the syringe, injection and calibration time, and incorrect synchronization of clocks of PET/CT and dose calibrator.

Therefore, it would be desirable to have a system and method for therapy planning, such as radiation therapy treatment planning, that benefits from the important information that can be derived from medical images including functional information, such as PET images and the like, but does not suffer from the limitations and uncertainties inherent in traditional planning methods, such as uncontrolled variability, such as created by user input or user variations.

SUMMARY OF THE INVENTION

The present invention overcomes the aforementioned drawbacks by providing a system and method for parameter-free, auto-segmentation. For example, the present invention may be used for radiotherapy target definition, by using a combination of up to three different stages that may include generation of multiple highly discriminate texture feature images, a parameter-free, non-connected region-Growing (NCRG) to determine a desired segmentation for each image yielding multiple region of interest (ROI), and determination of a tumor region using a synthesis and analysis algorithm. As described hereafter, this combination of stages may be referred to as a gradient assisted non-connected automatic region (GANAR) technique.

In accordance with one aspect of the invention, a method is disclosed for programming operation of a radiation therapy system to deliver radiation therapy to a subject. The method includes acquiring medical images of the subject including functional information and anatomical information about the subject and acquiring texture feature images. The method also includes using the medical images and the texture feature images, determining a plurality of segmentation surfaces by minimizing a relationship between a region growing algorithm that selects a region of interest (ROI) to determine a given segmentation surface and cost function for evaluating the given segmentation surface. The method further includes synthesizing the plurality of segmentation surfaces into a segmentation report and using information from the segmentation report to program operation of the radiation therapy system for a delivery of radiation therapy to the subject.

In accordance with another aspect of the invention, a system is disclosed for processing medical images of a subject. The system includes a communications connection configured to acquire medical images of the subject including functional information and anatomical information about the subject and a non-transitory storage medium having stored thereon texture feature images. The system includes a computer system configured to communicate with the communications connection to receive the medical images and communicate with the non-transitory storage medium to access the texture images. The computer system is also configured to determine, using the medical images and the texture feature images, a plurality of segmentation surfaces by iteratively adjusting a relationship between a region growing algorithm that selects a region of interest (ROI) to determine a given segmentation surface and cost function for evaluating the given segmentation surface. The computer system is further configured to generate a report using the plurality of segmentation surfaces indicating at least boundaries between anatomical structures with functional differences in the medical images.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
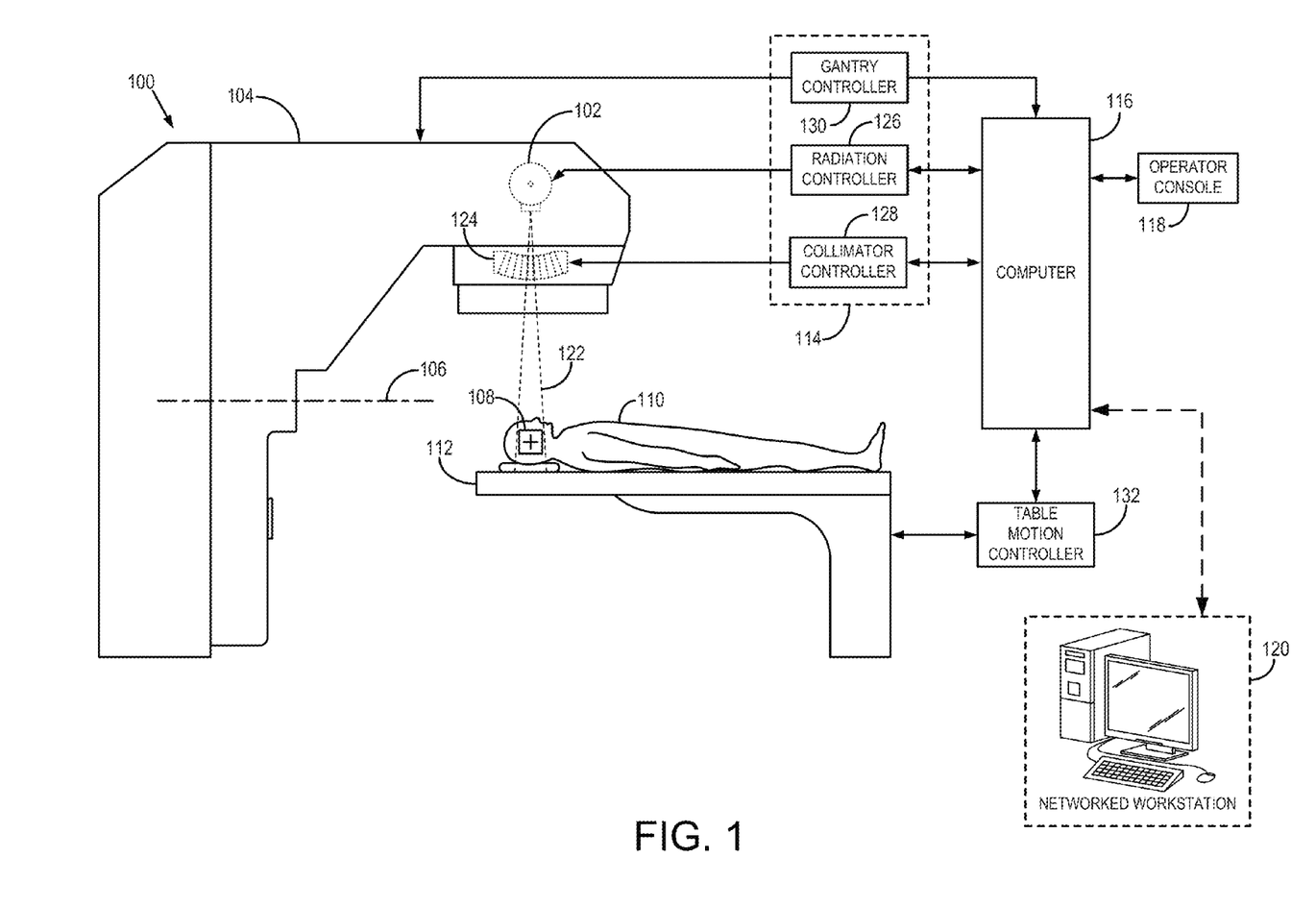
FIG. 1 is a schematic illustration of a radiation therapy system and computer system configured to in accordance with the present invention and designed to communicate with the radiation therapy system.

Referring to FIG. 1, an example of therapy system 100 is illustrated. In particular, an intensity-modulated radiation therapy ("IMRT") system 100 is illustrated. As will be described, the present invention provides systems and methods that can be used for therapy and medical procedure planning. In this regard, the present invention may be used with therapy system, such as an IMRT system, and other therapy systems, including other radiation therapy systems, such as stereotactic radiation systems (radiosurgery systems), particle therapy, and various other therapy and medical procedure planning.

The illustrated system 100 includes a radiation source 102, such as an x-ray source, that is housed at an end of a rotatable gantry 104 that rotates about a rotation axis 106. The rotatable gantry 104 allows the radiation source 102 to be aligned in a desired manner with respect to a target volume 108 in a subject 110 positioned on a patient table 112. A control mechanism 114 controls the rotation of the gantry 104 and the delivery of radiation from the radiation source 102 to the target volume 108. The system 100 includes a computer 116 that receives commands and scanning parameters from an operator via a console 118, or from a memory or other suitable storage medium or other networked system. That is, a networked workstation 120 may be coupled to the system 100. As will be described in further detail, the computer 116 or networked workstation 120 allows the operator to observe data, including images of the subject 110 that may be used to create, review, or modify a treatment plan.

The radiation source 102 produces a radiation beam 122, or "field," that is modulated by a collimator 124. The collimator 124 may include a multileaf collimator that is composed of a plurality of independently adjustable collimator leaves. In such a configuration, each leaf in the collimator 124 is composed of an appropriate material that inhibits the transmission of radiation, such as a dense radio opaque material, and may include lead, tungsten, cerium, tantalum, or related alloys.

The radiation source 102 is mounted on the rotatable gantry 104 that rotates about the rotation axis 106 so that the radiation beam 122 may irradiate the target volume 108 in the subject 110 from a variety of gantry angles, $\theta_i$. The radiation source 102 is controlled by a radiation controller 126 that forms a part of the control mechanism 114, and which provides power and timing signals to the radiation source 102.

A collimator controller 128, which forms a part of the control mechanism 114, controls the movement of each of the collimator leaves in and out of its corresponding sleeve. The collimator controller 128 moves the collimator leaves rapidly between their open and closed states to adjust the aperture shape of the collimator 124 and, therefore, the shape and fluence of the radiation beam 122. The collimator controller 128 receives instructions from the computer 116 to allow program control of the collimator 124.

A gantry controller 130, which forms a part of the control mechanism 114, provides the signals necessary to rotate the gantry 104 and, hence, to change the position of the radiation source 102 and the gantry angle, $\theta_i$, of the radiation beam 122 for the radiation therapy. The gantry controller 130 connects with the computer 116 so that the gantry 104 may be rotated under computer control, and also to provide the computer 116 with a signals indicating the gantry angle, $\theta_i$, to assist in that control. The position of the patient table 112 may also be adjusted to change the position of the target volume 108 with respect to the radiation source 102 by way of a table motion controller 132, which is in communication with the computer 116.

During operation of the system 100, a therapy plan is used to direct the system 100 to control components of the system 100, such as the radiation controller 126, collimator controller 128, gantry controller 130, and table motion controller 132 to carry out a radiation therapy plan. For example, the collimator controller 128 receives, from the computer 116, segmentation information indicating the aperture shape to be used for each gantry angle, $\theta_i$, during each sweep of the radiation source 102. The segmentations describe the intensity of the radiation beam 122 that is desired for each gantry angle, $\theta_i$. Likewise, the gantry controller 130 and table motion controller 132 receive location and position information to coordinate the location of the radiation beam 122 and the patient 110.

As will be described, the present invention provides a system and method that may be integrated with the computer 116 of the system 100 or used with other systems, such as the networked workstation 120, to create and implement medical plans, such as plans for therapies including radiation therapy plans, to be implemented with the system 100 of FIG. 1 or any of a variety of other medical treatment or therapy systems. Thus, all of the components of the system 100 and, in particular, the radiation controller 126, collimator controller 128, gantry controller 130, and table motion controller 132 may be controlled and operated based on the plans or reports generated using the present invention.

Figure 2:
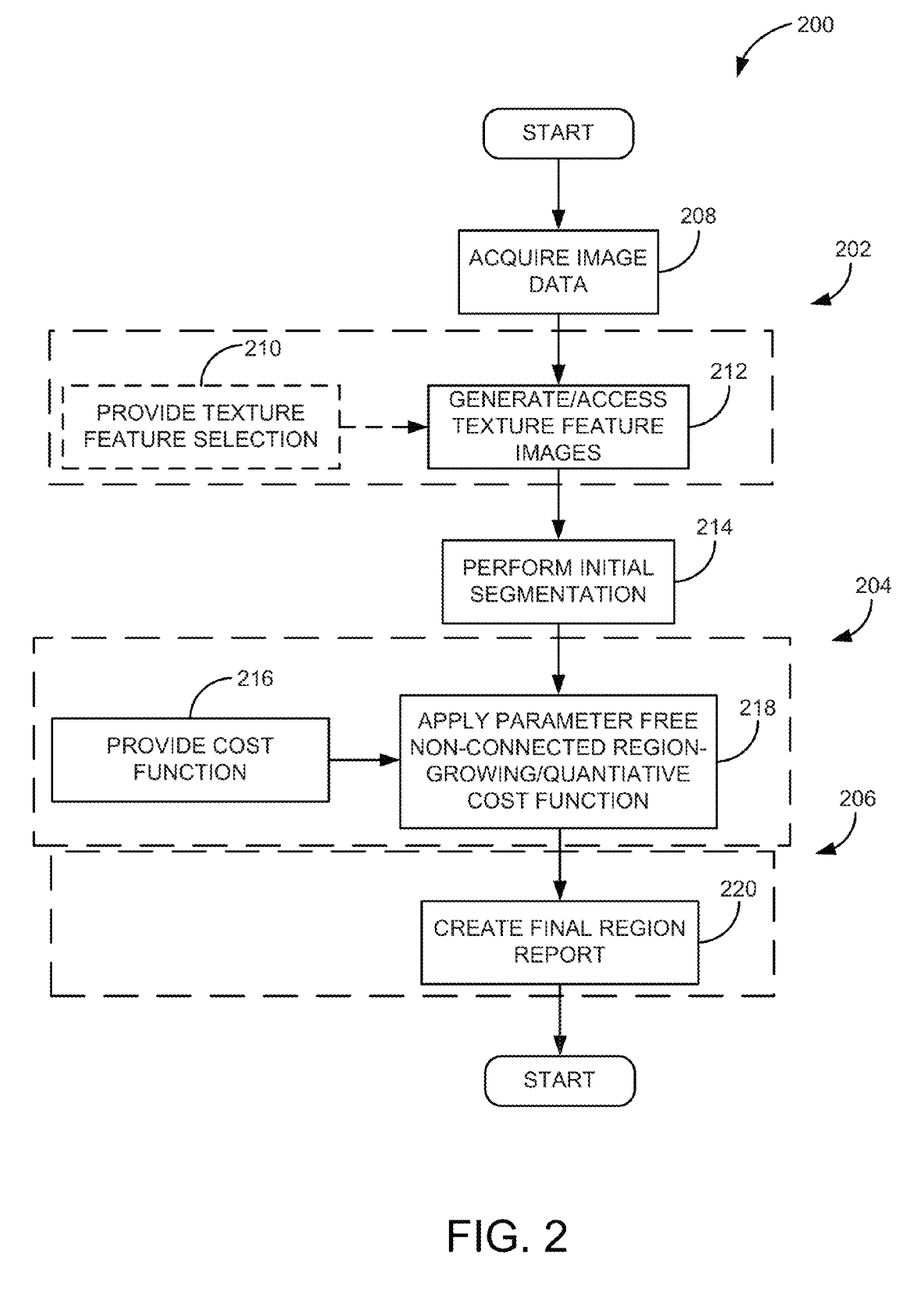
FIG. 2 is a flow chart setting forth exemplary stages and steps of a method in accordance with the present invention that may be used with the systems of FIG. 1.

Referring to FIG. 2, one implementation of the present invention can be described as a gradient assisted non-connected automatic region (GANAR) method including a plurality of steps 200 can be grouped into three different stages 202, 204, 206. The first stage 202 may include generation of multiple, such as five, highly discriminate texture feature images. The second stage 204 may include applying a parameter-free, non-connected, region-growing (NCRG) based on, for example, two assessment functions to determine a desired segmentation for each image yielding multiple, such as twelve, region of interest (ROI). The third stage 205 may include creating a report indicating the tumor region and/or other therapy planning indicators using an algorithm, such as a simultaneous truth and performance level estimation (STAPLE) algorithm. This report can be used for creating or information therefrom included in a radiation therapy plan.

More particularly, the process steps 200 begin at process block 208 with the acquisition of image data. The "acquisition" may include the acquiring and reconstructing of image data into images, such as PET images or any other imaging modality suitable for a given planning procedure. Also, the "acquisition" may include accessing previously acquired imaging data or images.

In accordance with one aspect of the invention, multiple highly discriminate texture feature images may be used, as will be described, to segment distinct properties of a given target in the images, such as a tumor, with the parameter-free, non-connected region-growing algorithm of the second stage 204.

The purpose of the first stage 202 is to identify texture features selections with desirable discriminate power between classes. In the following example, two classes may be used that correspond to tumor and background tissue. However, one of ordinary skill in the art will readily appreciate that other classes may be utilized for other medical procedures and procedure planning. The discriminatory power of images may be determined, for example, based on the Fisher's discriminate ratio (SFDR). Thus, in accordance with one aspect of the invention the texture features images may be designed to possess high-discriminatory, power between tumor and background structures. These features may include first-order (mean and median) and high-order (long run emphasis, long run low gray-level emphasis, and long run high gray-level emphasis). Thus, five images may be used that, together with the original raw image (for a total of six images), are then passed to process block 214 to perform an initial segmentation. However, other images are also contemplated.

Thus, in one configuration, five highly discriminate texture feature images may be used. At process block 210 multiple texture feature selections are provide that are used at process block 212 to generate texture features images.

In accordance with one implementation, an entire texture feature image may be used, unlike traditional uses of texture feature images, in which a feature bank is created from a training data set based on known lesion site and background. As such, the present invention does not require a training data set. Instead, texture feature images can be generated, for example, from a desired image set, such as 18F-FDG PET images, and used for segmentation. Once the texture features have been identified using a benchmark data set, these images can be reused for each new iteration of the process 200 for each new set of image data 208. Thus, generating a new texture feature is not necessary for each iteration and, instead, process block 212, may simply include accessing the texture features image(s).

Figure 3:
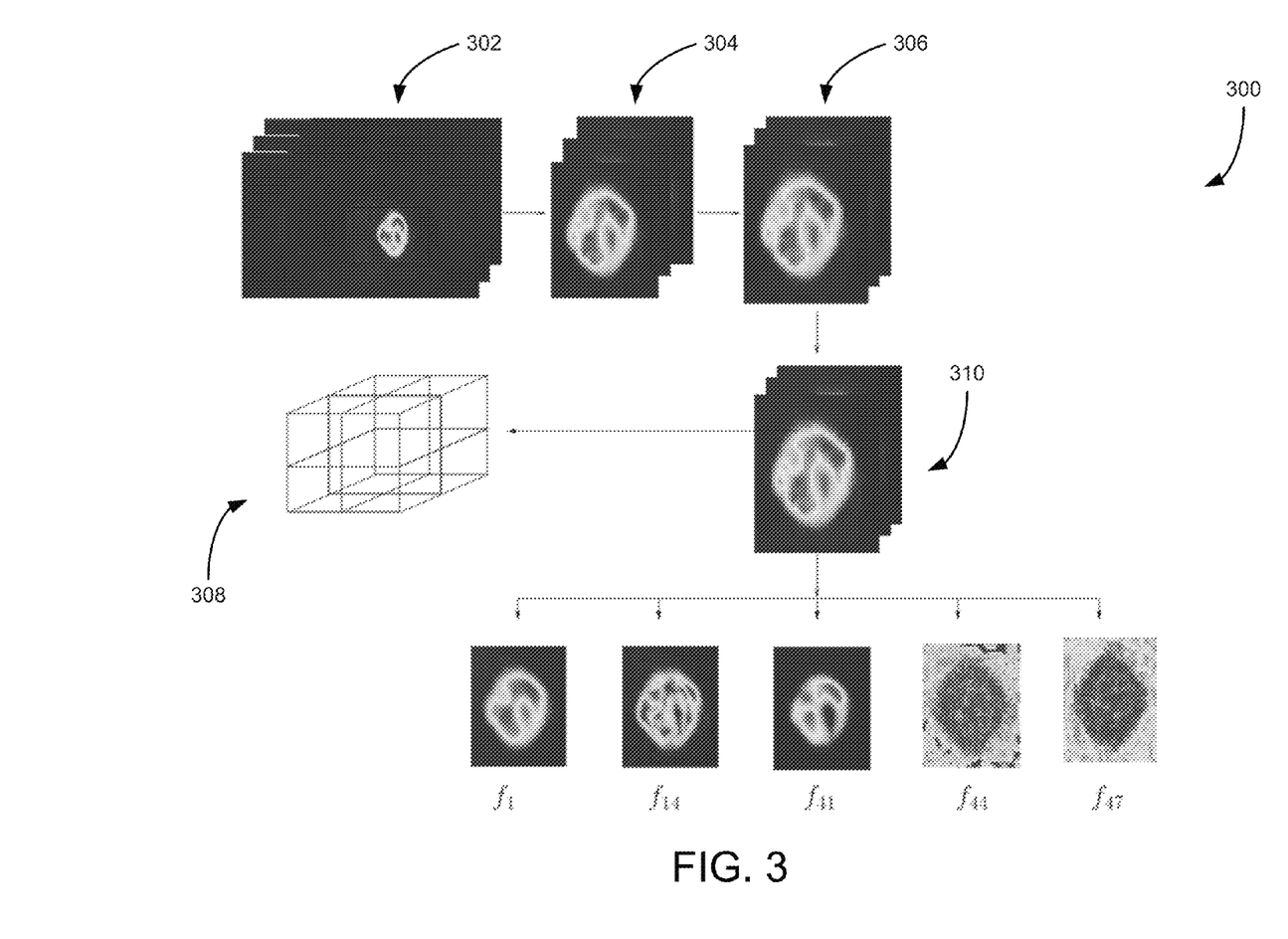
FIG. 3 is a schematic diagram of a process for texture feature image generation in accordance with the present invention.

Referring to FIG. 3, one example of a method 300 for creating or selecting texture images in accordance with the present invention is illustrated. The method 300 in this example uses patient diagnostic reports from PET images for tumor localization. Amira software (Visage Imaging) was used for tumor region identification to define, across a series of images, a tumor location 302, a ROI 304, and an ROI+ 306. In particular, a tumor location 302 may be, as shown, an axial slice with the tumor location. This can be correlated with an ROI 304. The tumor location 302 and ROI 304 were identified and a margin of four pixels was added to this ROI on the x and y axes to define the ROI+ 306, to ensure that the texture feature images are generated inside the region of interest. Fifty texture feature images were generated from the ROI+ 306 as part of the development process. The calculation of all features (except first-order features) was performed using the SUVs scaled to 256 intensity levels, assigning 0 to the minimum and 255 to the maximal intensity of the PET image. The texture feature images were generated on a voxel-by-voxel basis, taking the mean value obtained from 3 planes (or patches) of a 3×3×3 cube 308 centered on each PET image voxel of the ROI+ 306. In this way, each voxel of the ROI+ 306 was transformed into a texture feature voxel, whose value represents the average texture feature calculated with all the 3 local patches (axial, coronal and sagittal) of the 3×3×3 cube around the current voxel 310. For example, some texture feature images are illustrated that correspond to the mean (first-order) f1, the sum average (second-order feature calculated from the gray level co-occurrence matrix (GLCM)) f14, the long run low gray-intensity level (high-order feature calculated from the gray level run length matrix (GLRLM)) f41, the large number emphasis (high-order feature calculated from the neighboring gray level dependence matrix (NGLDM)) f44, and the entropy (high-order feature calculated from the NGLDM) f47. The equations used for these feature calculations, which are exemplary only are:

TABLE 1

Description of first-order texture features.
In this table p(i, j) is the intensity level extracted
from the patch. k is the size of the patch, N is the number of
elements in the patch, L is the highest intensity value in the patch
and Hi(i) is the value of the probability histogram for intensity value i.

| Feature | Feature Options |
|---|---|
| Mean | $f_1 = \sum_{i=1}^{k}\sum_{j=1}^{k} \frac{p(i,j)}{N} = \mu$ |
| Median | $f_2$** |
| Variance | $f_3 = \sum_{i=1}^{k}\sum_{j=1}^{k} \frac{(p(i,j) - \text{mean})^2}{N-1} = \sigma^2$ |
| Coefficient of variation | $f_4 = \frac{\sqrt{\sigma^2}}{\text{mean}}$ |

TABLE 1-continued

Description of first-order texture features.
In this table p(i, j) is the intensity level extracted from the patch. k is the size of the patch, N is the number of elements in the patch, L is the highest intensity value in the patch and Hi(i) is the value of the probability histogram for intensity value i.

| Feature | Feature Options |
|---|---|
| Skewness | $f_5 = \sum_{i=1}^{k} \sum_{j=1}^{k} \frac{(p(i,j) - \mu)^3}{N * \sigma^3}$ |
| Kurtosis | $f_6 = \sum_{i=1}^{k} \sum_{j=1}^{k} \frac{(p(i,j) - \mu)^4}{N * \sigma^4} - 3$ |
| Energy | $f_7 = \sum_{i}^{L} H(i)^2$ |
| Entropy | $f_8 = \sum_{i}^{L} H(i) * \log H(i)$ |

The median ($f_2$) is calculated by ordering the intensity values from lowest to highest and since the patch is an array of odd numbers, the median value is the middle number.

TABLE 2

Description of second-order texture features from the gray level co-occurrence matrix (GLCM). In this table p(i, j) is the GLCM and it is normalized by its sum $\left(T = \sum_{i,j} p(i,j)\right)$. $p_x(i) = \sum_{j=1}^{N_g} P(i,j)$ is the ith entry in the matrix obtained by summing the rows of p(i, j). $N_g$ is the number of gray levels in I, $\mu_x$, $\mu_y$, $\sigma_x$ and $\sigma_y$ are the mean and standard deviations of $p_x$ and $p_y$, respectively.

| Feature | Feature equations |
|---|---|
| Angular Moment | $f_9 = \frac{1}{T} \sum_{i}^{N_g} \sum_{j}^{N_g} (p(i,j))^2$ |
| Contrast | $f_{10} = \frac{1}{T} \sum_{n=0}^{N_g - 1} n^2 p_{x-y}(n)$ |
| Correlation | $f_{11} = \frac{1}{T} \frac{\sum_{i}^{N_g} \sum_{j}^{N_g} (i \times j) p(i,j) - \mu_x \mu_y}{\sigma_x \sigma_y}$ |
| Sum of squares variance | $f_{12} = \frac{1}{T} \sum_{i}^{N_g} \sum_{j}^{N_g} (i - \mu)^2 p(i,j)$ |
| Inverse difference moment | $f_{13} = \frac{1}{T} \sum_{i}^{N_g} \sum_{j}^{N_g} \frac{p(i,j)}{1 + (i-j)^2}$ |
| Sum average | $f_{14} = \frac{1}{T} \sum_{i=2}^{2N_g} i p_{x+y}(i)$ |
| Sum variance | $f_{15} = \frac{1}{T} \sum_{i=2}^{2N_g} (i - f_{16}) p_{x+y}(i)$ |

TABLE 2-continued

Description of second-order texture features from the gray level co-occurrence matrix (GLCM). In this table p(i, j) is the GLCM and it is normalized by its sum $\left(T = \sum_{i,j} p(i,j)\right)$. $p_x(i) = \sum_{j=1}^{N_g} P(i,j)$ is the ith entry in the matrix obtained by summing the rows of p(i, j). $N_g$ is the number of gray levels in I, $\mu_x$, $\mu_y$, $\sigma_x$ and $\sigma_y$ are the mean and standard deviations of $p_x$ and $p_y$, respectively.

| Feature | Feature equations |
|---|---|
| Sum entropy | $f_{16} = \frac{1}{T} \sum_{i=2}^{2N_g} p_{x+y}(i) \log p_{x+y}(i)$ |
| Entropy | $f_{17} = -\frac{1}{T} \sum_{i}^{N_g} \sum_{j}^{N_g} p(i,j) \log(p(i,j))$ |
| Difference variance | $f_{18} = \frac{1}{T} \sigma^2 \{p_{x-y}(k)\}$ |
| Difference entropy | $f_{19} = -\frac{1}{T} \sum_{i=0}^{N_g - 1} p_{x-y}(i) \log(p_{x-y}(i))$ |

TABLE 3

Description of second-order texture features from the gray level co-occurrence matrix (GLCM). In this table p(i, j) is the GLCM and it is normalized by its sum $\left(T = \sum_{i,j} p(i,j)\right)$. $p_x(i) = \sum_{j=1}^{N_g} P(i,j)$ is the ith entry in the matrix obtained by summing the rows of p(i, j). $N_g$ is the number of gray levels in I, $\mu_x$, $\mu_y$, $\sigma_x$ and $\sigma_y$ are the mean and standard deviations of $p_x$ and $p_y$, respectively.

| Feature | Feature equations |
|---|---|
| Info. measure of correlation | $f_{20} = \frac{1}{T} \frac{HXY - HXY1}{\max(HX, HY)}$ and $f_{21} = \frac{1}{T} \sqrt{(1 - \exp(-2(HXY2 - HXY)))}$ |
| Max. correlation coefficient | $f_{22} = $ (Second largest eigenvalue Q), $Q(i,j) = \frac{1}{T} \sum_{k} \frac{p(i,k) p(j,k)}{p_x(i) p_y(k)}$ |
| Maximal probability | $f_{23} = \frac{1}{T} \max(p(i,j))$ |
| Diagonal moment | $f_{24} = \frac{1}{T} \sum_{i}^{N_g} \sum_{j}^{N_g} |i - j|(i + j - \mu_x - \mu_y) p(i,j)$ |
| Dissimilarity | $f_{25} = \frac{1}{T} \sum_{i} \sum_{j} |i - j| p(i,j)$ |
| Difference energy | $f_{26} = \frac{1}{T} \sum_{n} p_{x-y}^2(n)$ |
| Inertia | $f_{27} = \frac{1}{T} \sum_{i} \sum_{j} (i - j)^2 p(i,j)$ |

TABLE 3-continued

Description of second-order texture features
from the gray level co-occurrence matrix (GLCM).
In this table p(i, j) is the GLCM and it is normalized by its sum
$\left(T = \sum_{i,j} p(i, j)\right)$. $p_x(i) = \sum_{j=1}^{N_g} P(i, j)$ is the ith entry in the matrix obtained
by summing the rows of p(i, j). $N_g$ is the number of gray levels in I, $\mu_x$, $\mu_y$, $\sigma_x$ and $\sigma_y$ are the mean and standard deviations of $p_x$ and $p_y$, respectively.

| Feature | Feature equations |
|---|---|
| Inverse difference moment | $f_{28} = \frac{1}{T}\sum_{i}^{N_g}\sum_{j}^{N_g} \frac{p(i, j)}{1 + (i - j)}$ |
| Sum energy | $f_{29} = \frac{1}{T}\sum_{n} p_{x+y}^2(n)$ |
| Cluster shade | $f_{30} = \frac{1}{T}\sum_{i}^{N_g-1}\sum_{j}^{N_g-1} (i + j - \mu_x - \mu_j)^3 p(i, j)$ |
| Cluster prominence | $f_{31} = \frac{1}{T}\sum_{i}^{N_g-1}\sum_{j}^{N_g-1} (i + j - \mu_x - \mu_j)^4 p(i, j)$ |

TABLE 4

Description of high-order texture features
using the gray level run length matrix (GLRLM).
In this table z(i, j) is the GLRLM. $N_g$: is the
number of gray levels in I and $N_r$ is the number of different
run lengths that occur in the image such that the GLRLM is $N_g \times N_r$ size.

$$M = \sum_{i=1}^{N_g}\sum_{j=1}^{N_r} z(i, j)$$

| Feature | Feature equations |
|---|---|
| Short run emphasis | $f_{32} = \sum_{i=1}^{N_g}\sum_{j=1}^{N_r} \frac{z(i, j)}{j^2}$ |
| Long run emphasis | $f_{33} = \sum_{i=1}^{N_g}\sum_{j=1}^{N_r} z(i, j)j^2$ |
| Gray-level non-uniformity | $f_{34} = \sum_{i=1}^{N_g}\left(\sum_{j=1}^{N_r} z(i, j)\right)^2$ |
| Run length non-uniformity | $f_{35} = \sum_{j=1}^{N_r}\left(\sum_{i=1}^{N_g} z(i, j)\right)^2$ |
| Run percentage | $f_{36} = \sum_{i=1}^{N_g}\sum_{j=1}^{N_r} z(i, j)/Z$ |
| Low gray-level run emphasis | $f_{37} = \sum_{i=1}^{N_g}\sum_{j=1}^{N_r} \frac{z(i, j)}{i^2}$ |
| High gray-level run emphasis | $f_{38} = \sum_{i=1}^{N_g}\sum_{j=1}^{N_r} z(i, j)i^2$ |

TABLE 4-continued

Description of high-order texture features
using the gray level run length matrix (GLRLM).
In this table z(i, j) is the GLRLM. $N_g$: is the
number of gray levels in I and $N_r$ is the number of different
run lengths that occur in the image such that the GLRLM is $N_g \times N_r$ size.

$$M = \sum_{i=1}^{N_g}\sum_{j=1}^{N_r} z(i, j)$$

| Feature | Feature equations |
|---|---|
| Short run low gray-level emphasis | $f_{39} = \sum_{i=1}^{N_g}\sum_{j=1}^{N_r} \frac{z(i, j)}{i^2 j^2}$ |
| Short run high gray-level emphasis | $f_{40} = \sum_{i=1}^{N_g}\sum_{j=1}^{N_r} \frac{z(i, j)i^2}{j^2}$ |
| Long run low gray-level emphasis | $f_{41} = \sum_{i=1}^{N_g}\sum_{j=1}^{N_r} \frac{z(i, j)j^2}{i^2}$ |
| Long run high gray-level emphasis | $f_{42} = \sum_{i=1}^{N_g}\sum_{j=1}^{N_r} z(i, j)i^2 j^2$ |

TABLE 5

Description of high-order texture features using the
neighboring gray level dependence matrix (NGLDM).
In this table q(i, s) is the NGLDM. $N_g$: is the
number of gray levels in I and $N_{DM} = \sum_{i=1}^{N_g}\sum_{s=1}^{S} q(i, s)$

| Feature | Feature equations |
|---|---|
| Small number emphasis | $f_{43} = \frac{1}{N_{DM}}\sum_{i=1}^{N_g}\sum_{s=1}^{S} \frac{q(i, s)}{s^2}$ |
| Large number emphasis | $f_{44} = \frac{1}{N_{DM}}\sum_{i=1}^{N_g}\sum_{s=1}^{S} q(i, s)s^2$ |
| Number non-uniformity | $f_{45} = \frac{1}{N_{DM}}\sum_{i=1}^{N_g}\left(\sum_{s=1}^{S} q(i, s)\right)^2$ |
| Second moment | $f_{46} = \frac{1}{N_{DM}}\sum_{i=1}^{N_g}\sum_{s=1}^{S} (q(i, s))^2$ |
| Entropy | $f_{47} = -\frac{1}{N_{DM}}\sum_{i=1}^{N_g}\sum_{s=1}^{S} q(i, s) \log q(i, s)$ |

Referring again to FIG. 2, in stage two 204, each of the texture features images and raw images may be segmented based on at least one cost function that is provided at process block 216. Again, as stated, the above-described process for selecting or creating texture features images need not be repeated unless new classes or new features are desired or identified. Thus, in many implementations, the process begins at the second stage 204 with the raw images and the texture features images in hand.

In one implementation of the second stage 204, it is contemplated that the images may be segmented twice, based on two distinct cost functions that quantify desirable features of the optimal segmentation. Continuing with the non-limiting example presented above of five texture features images and a set of raw medical images, 12 segmentations (6 images times 2 cost functions) may be treated completely independently of all the others. Each segmentation may involve the combination of two methods, such as a non-connected region-growing (NCRG) algorithm and a quantitative cost function. One implementation an NCRG algorithm is provided by C. Revol and M. Jourlin. A new minimum variance region growing algorithm for image segmentation. Pattern Recognition Letters, 18(3), 1997, which is incorporated herein by reference in its entirety. An implementation of a quantitative cost function is provided by D. Mumford and J. Shah. Optimal Approximations By Piecewise Smooth Functions And Associated Variational-Problems. Communications on Pure and Applied Mathematics, 42(5):577-685, 1989, which is incorporated herein by reference.

Thus, process block 218 can be conceptualized as the combination of two distinct methods into a complementary and focused process. That is, a first method uniquely determines a segmentation surface given a value of the maximum inhomogeneity and a second a method evaluates cost functions to be minimized given a segmentation surface. The second stage 204 combines these two in a non-linear minimization routine with an inhomogeneity parameter, σ, being the sole parameter that can be discarded when creating the ultimate report of the segments. In this way, the second stage 204 produces multiple (using the example above of 6 images, twelve) distinct contours for each image that serve as the input for the third stage 206. Thus, as will be further detailed, using the medical images and the texture feature images, the second stage 204 is able to determine a plurality of segmentation surfaces by minimizing a relationship between the region growing algorithm that selects a region of interest (ROI) to determine a given segmentation surface and cost functions for evaluating the given segmentation surface. Put another way, the relationship between the region growing algorithm and the cost function is through the inhomogeneity parameter. The inhomogeneity parameter is used by the region growing algorithm to determine a largest segmentation surface that yield a degree of inhomogeneity less than a maximum acceptable measure of inhomogeneity and is used by the cost function to evaluate the largest segmentation surface to control inter-voxel and intra-voxel variances relative to the largest segmentation surface.

Specifically, the region growing method begins with a quantitative measure of the maximum acceptable degree of inhomogeneity (σ) and determines the largest segmentation contours (in three dimensions, the segmentation surface) that yield a degree of inhomogeneity less than this maximum. On the other hand, the cost function method begins with segmentation contours and calculates the value of particular expressions based on those contours.

Unlike the above-referenced method by Revolt et al., which chose the voxel value standard deviation as the estimator for region inhomogeneity, the present disclosure may use the coefficient of variation, the standard deviation scaled by the mean value. Thus, at each iteration of the region growing process, the criterion C(R)=std(R)/mean(R) less thank or equal to σ is evaluated. Use of the coefficient of variation causes C(R) to be dimensionless, and independent of the overall image intensity.

Figure 4:
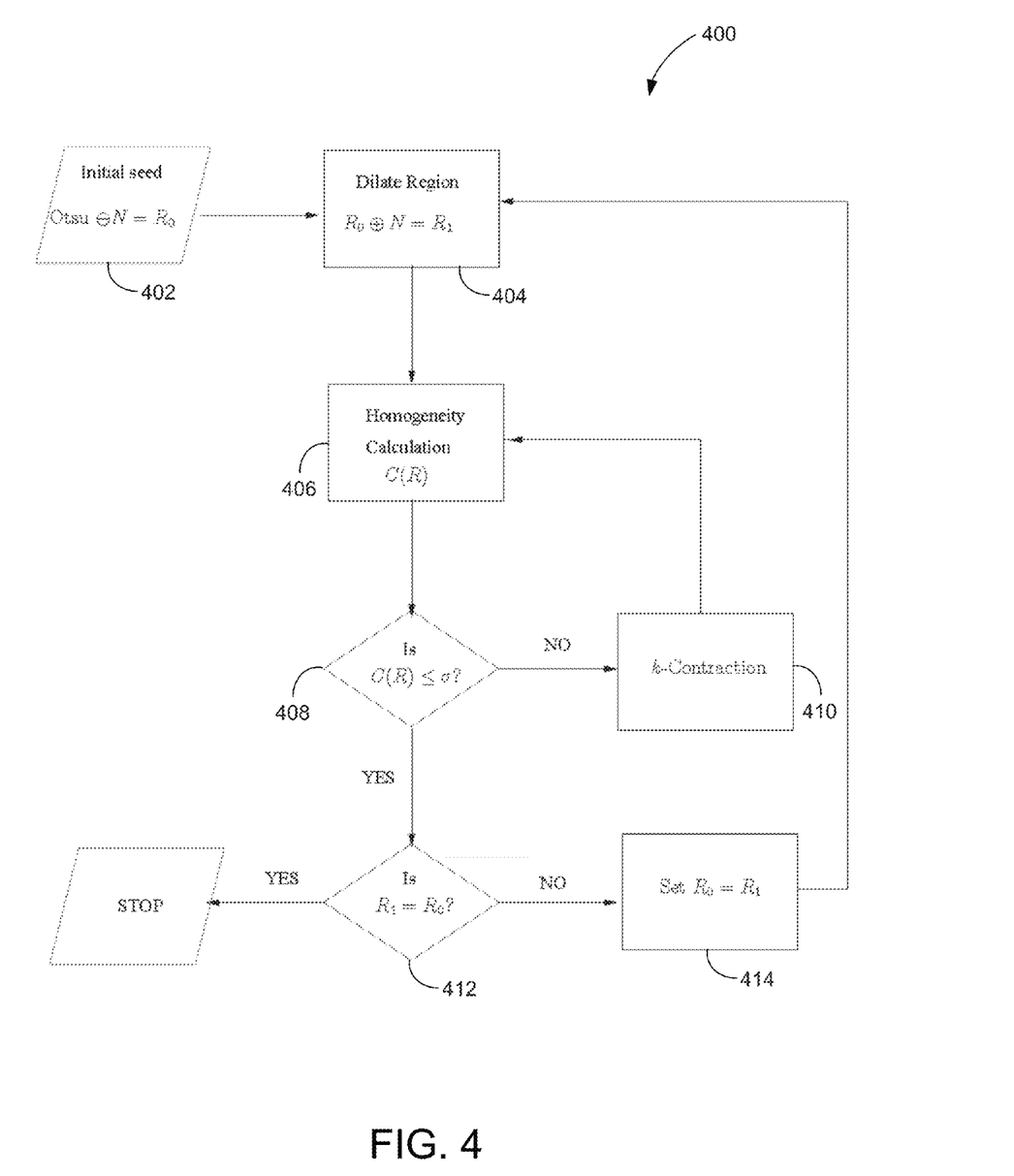
FIG. 4 is a flow chart setting forth the steps of a non-connected region growing (NCRG) algorithm in accordance with the present invention.

Referring to FIG. 4, a process 400 for NCRG begins with generation of the initial seed region 402. ⊖ and ⊕ are symbols for erosion and dilation operations, respectively. As will be described, C(R)=std(R)/mean(R) and σ is the stopping criterion. The region can be as small as a one voxel to initialize the algorithm. However, in order to speed up the process, a method such as described in Nobuyuki Otsu. A Threshold Selection Method from Gray-Level Histograms. IEEE Transactions On Systems, Man, And Cybernetics, 9(1), 1979, which is incorporated herein by reference in its entirety, may be used, followed by an erosion operation to define the initial region R0. The erosion operation may be used to ensure that the initial region is closer to the ROI.

At process block 404, a dilation operation may be applied to R0. This operation may use a structuring element that adds pixels to the binary mask obtained from process block 402. This new region is named R1. It is worth noticing that in the first iteration this step will restore R0 back to the original segmentation, such as provided when, for example, the above method by Otsu is utilized.

At process block 406, a calculation of the coefficient of variation C(R1) is performed. Thereafter, at decision block 408, $R_1$ is checked to see if it is homogeneous with respect to σ. That is, whether $C(R_1)$ is less than or equal to σ. If not, then the $R_1$ region is trimmed using a left k-contraction method at process block 410. This loop is repeated until a homogeneous region is produced, which satisfies the criteria C(R) less than σ.

Once a homogeneous region is produced, at decision block 412, the new region is checked to determine if it is the same as the one obtained in the previous iteration. If not, then $R_1$ is set as a new seed at process block 414 and the process repeats. The algorithm stops when the regions are the same after two consecutive iteration, which means that the process of dilation+k-contraction results in the same region.

One potential drawback of NCRG, as with any parametric algorithm, is that it is necessary to establish the parameter, in this case σ. However, there is not a priori rule or prescription on what is the best value for σ. Accordingly, the present disclosure provides two assessment functions that can be used to define the a parameter.

The assessment functions used may be, for example, a version of those provided by Mumford and Shah functional. Because of the discrete nature of the digital images that form the basis of the overall analysis, for example, as provided in process block 208 of FIG. 2, it may be advantageous to use a discrete approach for $f_1$ and $f_2$ to obtain the characteristics of the ROI. These functions to define the σ parameter are expressed as:

$$f_1(\sigma) = \sum_{x \in R(\sigma)} (I(x) - \mu_R)^2 + \sum_{x \in R^C(\sigma)} (I(x) - \mu_R^C)^2 \qquad \text{Eqn. 1}$$

$$f_2(\sigma) = -\sum_{x \in \partial R(\sigma)} |\nabla I(x)|^2$$

where, $$R^C = \{x \mid x \notin R\}$$

$$\mu_R = \text{mean } [I(x)] \forall\, x \notin R$$

$$\mu_R^C = \text{mean } [I(x)] \forall\, x \notin R;$$

and $f_1$ evaluates the total variance of the foreground and background, favoring regions which closely resemble the underlying images mean values and $f_2$ aims to assess the edges (steep transitions) of the ROI.

The first expression ($f_1$) is the sum of the voxel value variances inside and outside the contours. The process is built upon the realization that tumor-background contrast is the major source of voxel value variance, and the sum of the variance inside plus the variance outside is minimized by accurately separating the two regions. The second expression ($f_2$) a calculation of the total gradient of the voxel values in each of the contour voxels. These processes can be combined into a minimization problem by searching for the minimum of its negative. In this regard, the evaluation of the segmentation surface from the region growing considers inter-voxel and intra-voxel variances. This process is built upon the realization that the result can be used as a maximum for the optimal segmentation.

A cost function evaluation begins with segmentation contours from NCRG and calculates the value of particular expressions based on those contours. That is, referring to FIG. 5, a process 500 for the evaluation of the regions through the assessment functions is performed a region for each a 502. That is, at process block 504, NCRG defines a region for each $\sigma$, resulting in a family of regions R($\sigma$) parameterized by the $\sigma$ parameter. At process block 506, two cost functions are used to evaluate the regions. That is, the assessment functions are used to evaluate the regions (R($\sigma$)) for each $\sigma$ and possess a minimum for some value $\sigma c$, whose region R($\sigma c$) defines the optimal contour.

Figure 5:
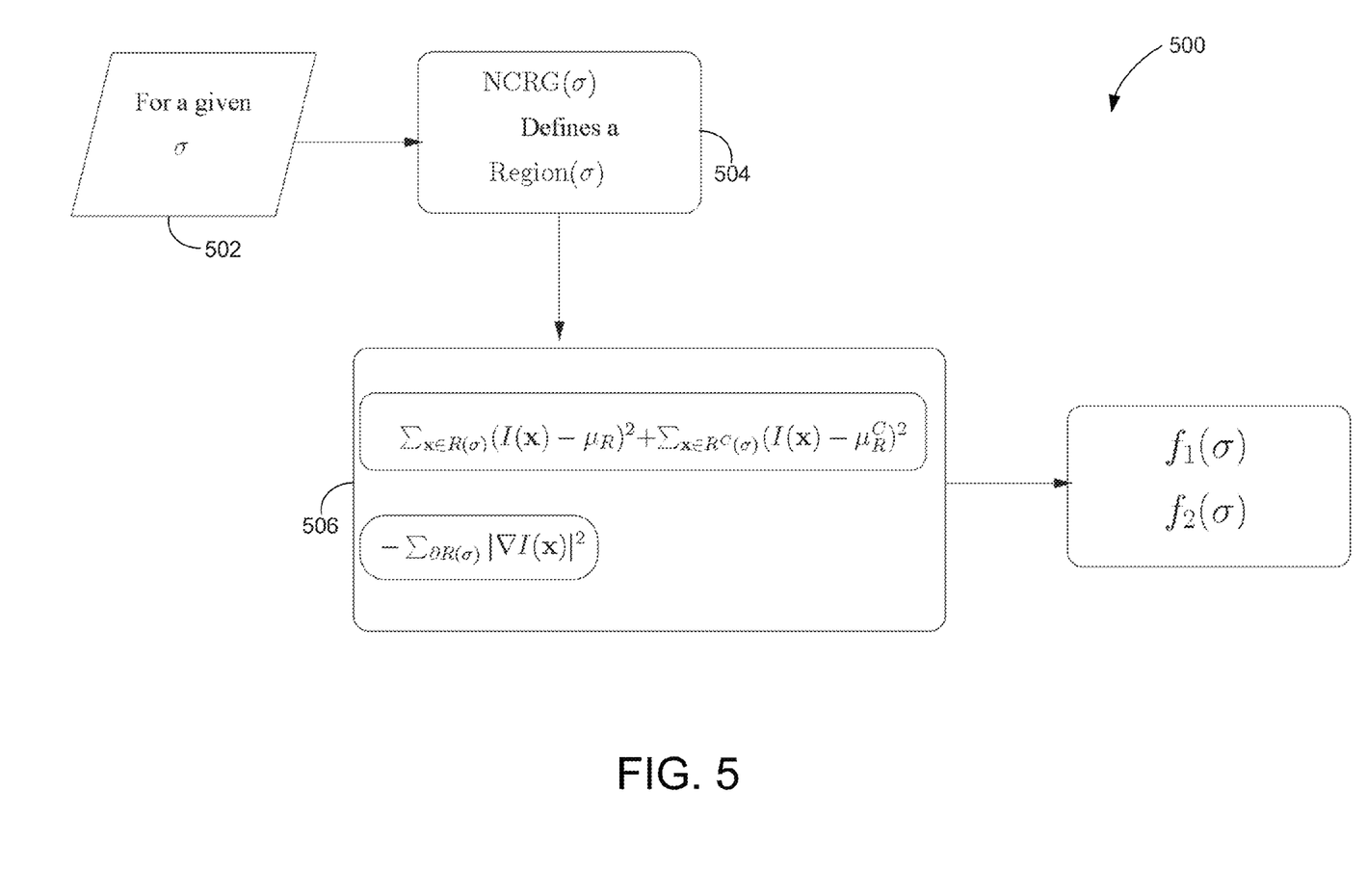
FIG. 5 is a flow chart setting forth the steps of a region assessment process in accordance with the present invention.

As an example, these functions may be minimized (optimization process) individually using a Matlab function known as fminsearch, which requires and initial guess $\sigma_{guess}$ and the function to be minimized. The initial guess used in each call to fminsearch is taken as the coefficient that corresponds to the region given by an Otsu segmentation.

Referring again to FIG. 2, the output of the process described with respect to the second stage 204 is passed to the third stage 206 to, at process block 220, create a final region report by synthesizing the plurality of segmentation surfaces into a the report. Ultimately, then, the information from the report is used to program operation of the radiation therapy system, such as described with respect to FIG. 1, for a delivery of radiation therapy to the subject.

Using the example of a set of PET images and five texture feature images, optimizing $f_1$ and $f_2$ will lead to two different segmented regions from the PET images and ten different segmented regions from the from the texture feature images, for a total of twelve regions. The final region can be defined by synthesizing this information. For example, an expectation maximization algorithm for simultaneous truth and Performance level estimation (STAPLE) method may be used, as described in S. K. Warfield, K. H. Zou, and W. M. Wells. Simultaneous truth and performance level estimation (STAPLE): An algorithm for the validation of image segmentation. IEEE Transactions on Medical Imaging, 23(7), 2004, which is incorporated herein by reference in its entirety.

Figure 6:
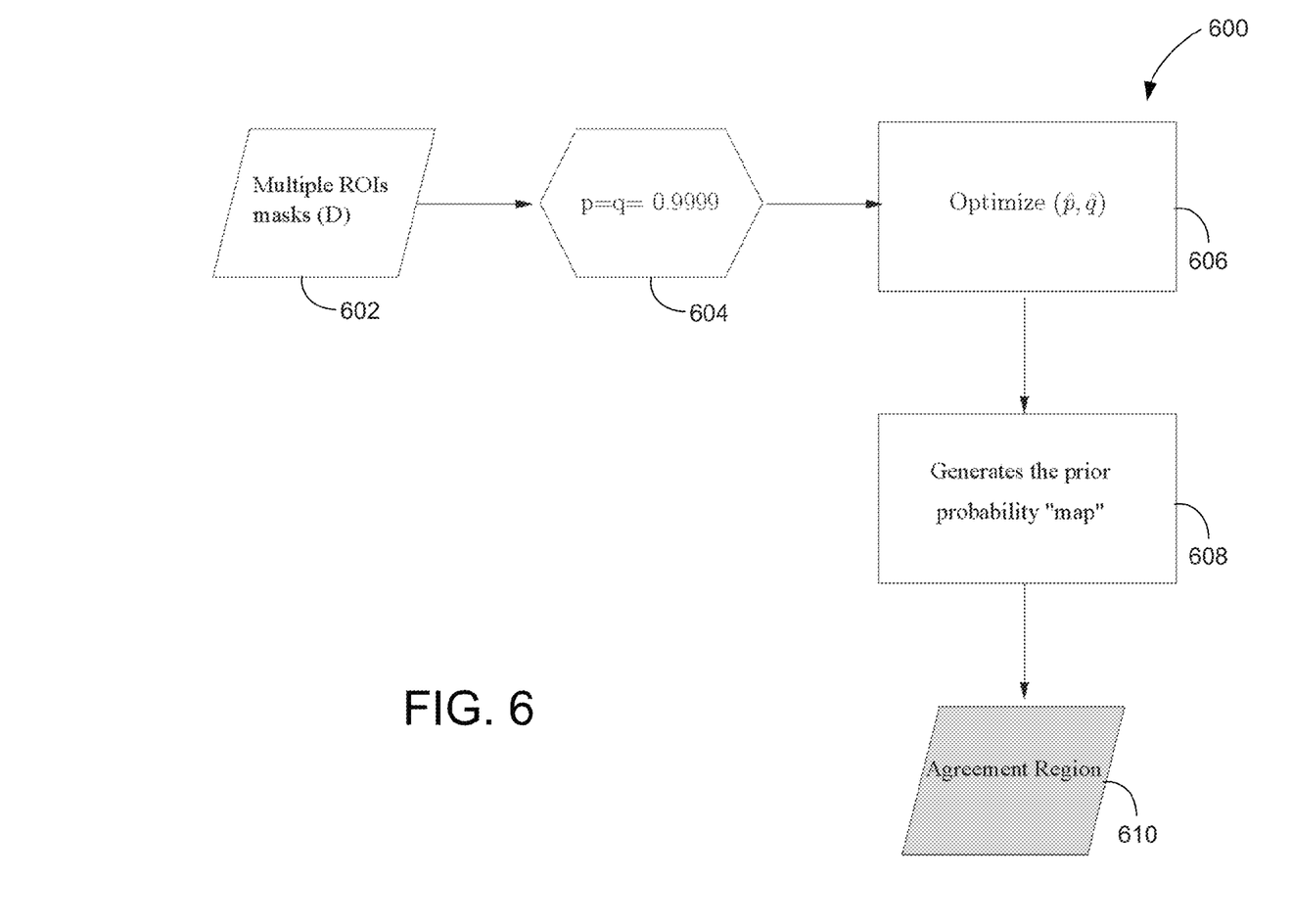
FIG. 6 is a flow chart setting forth the steps of a process for final region determination in accordance with the present invention.

The STAPLE algorithm can be used to collect the segmentations, in this case the segmentations, as described above, are from PET and texture feature images after f1 and f2 optimization, and calculate a probabilistic estimate of the true segmentation. Thus, referring to FIG. 6, in accordance with the present implementation 600, the STAPLE method is used to estimate the performance level of the segmentation by maximizing the likelihood function P(D, T/p, q), that is, $$(\hat{p}, \hat{q}) = \arg\max_{p,q} P(D, T \mid p, q); \qquad \text{Eqn. 2}$$

where D is defined as a matrix describing the binary decisions made by each of the S segmentations, given by N×S and (N is the number of voxels contained in the segmented images). Thus, as described above, the output of the second stage can be used to define the matrix D 602 describing the binary decisions made by each of the S segmentations. Referring to step 604, p and q are the vectors representing the sensitivity (fraction of true positives) and specificity (fraction of true negatives) of the segmented regions S obtained from the parameter free NCRG described above. The sensitivity and specificity parameters characterize the performance of each segmented region, which are set in this work initially to 0.9999. T is a vector of N elements representing the unknown binary true segmentations, where each voxel has a value of 1 if it is part of the region of interest, and a value of 0 otherwise. At step 606, ^p, ^q are optimized and used, at process block 608 to generate the prior probability map that givens rise, at block 610 to final region. At process block 608 the user may provide a confidence level for computing the final region.

Therefore, the present invention provides a system and method for image-based auto-segmentation that may be used, for example, in medical planning procedures. The method, which may be referred to as the gradient assisted non-connected automatic region (GANAR) method, generates texture feature images to segment distinct properties of the tumor with a parameter free non-connected region-growing algorithm. An expectation-maximization algorithm is used to define the final region of interest. The generation of texture feature images avoids texture feature data banks to characterize lesions and normal tissue, making the method applicable to any lesion site. By incorporating texture feature information and automatic parameter optimization, the GANAR method is less sensitive to acquisition mode and reconstruction parameters. The present invention is also beneficial for treatment response assessment, since accurate tumor delineation will lead to more reliable quantitative analysis such as SUV-based metrics.

The present invention is particularly advantageous because it provides systems and methods for segmentation that requires less or no user intervention and that is parameter free. The present invention advantageously does not depend on any parameter, and therefore there is no need for system-dependent optimization procedures as it is the case for other segmentation techniques.

The accuracy of the GANAR systems and methods was assessed using PET-based Monte Carlo phantom as well as clinical data. As it was shown in this study using PET-based simulated real lesions, GANAR was able to successfully deal with irregular lesion shapes and variable activity concentrations and performed better than the threshold-based, gradient-based, or region-growing segmentation methods. The techniques can be extended to more than two classes to allow modeling a combination of inhomogeneous regions within a given gross tumor volume. In this regard, the present invention can further enhance the use of GANAR for dose painting.

The robustness of the above-described systems and methods was assessed using FDG PET/CT images of twenty patients acquired in 2D and 3D modes, and reconstructed with varying parameters. In total, ten reconstructions used within clinical settings per patient were used. The Dice, sensitivity, positive predictive value, and Modified Hausdorff Distance (MHD) metrics were used to quantify the robustness. GANAR results were compared against threshold-based, gradient-based and region-growing methods. The present invention had the highest Dice coefficient, sensitivity, PPV values (above 0.9), and small MHD (below 0.1 cm), confirming its robustness to PET acquisition modes and variation of reconstruction parameters. These results are valid across different tumor sites such as lung, epiglottis, adrenal gland, esophagus and metastasis. Based on these findings it was demonstrated that the GANAR systems and methods are more robust than threshold-based, gradient-based and region-growing methods under varying reconstruction parameters.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for programming operation of a radiation therapy system to deliver radiation therapy to a subject, the method comprising:
    acquiring medical images of the subject including functional information and anatomical information about the subject;
    generating texture feature images using the acquired medical images;
    using the medical images and the texture feature images, determining a plurality of segmentation surfaces by minimizing a relationship between a region growing algorithm that selects a region of interest (ROI) to determine a given segmentation surface and cost function for evaluating the given segmentation surface;
    synthesizing the plurality of segmentation surfaces into a segmentation report; and
    using information from the segmentation report to program operation of the radiation therapy system for a delivery of radiation therapy to the subject.

2. The method of claim 1 wherein the relationship between the region growing algorithm and the cost function is defined by a single variable.

3. The method of claim 2 wherein the single variable is an inhomogeneity parameter.

4. The method of claim 1 wherein the relationship between the region growing algorithm and the cost function is defined by an inhomogeneity parameter that is used by the region growing algorithm to determine a largest segmentation surface that yield a degree of inhomogeneity less than a maximum acceptable measure of inhomogeneity and is used by the cost function to evaluate the largest segmentation surface to control inter-voxel and intra-voxel variances relative to the largest segmentation surface.

5. The method of claim 4 wherein the inhomogeneity parameter is disregarded when synthesizing the plurality of segmentation surfaces into a segmentation report.

6. The method of claim 1 wherein the segmentation report forms a portion of a radiation therapy plan.

7. The method of claim 1 wherein synthesizing the plurality of segmentation surfaces into a segmentation report includes calculating a probabilistic estimate of a probabilistic segmentation surface from the plurality of segmentation surfaces.

8. The method of claim 1 wherein the synthesizing the plurality of segmentation surfaces into a segmentation report includes performing an expectation maximization algorithm.

9. The method of claim 8 wherein the expectation maximization algorithm includes a simultaneous truth and performance level estimation (STAPLE) algorithm.

10. The method of claim 1 wherein the texture feature images are entire texture feature images.

11. A system for processing medical images of a subject, the system comprising:
    a communications connection configured to acquire medical images of the subject including functional information and anatomical information about the subject;
    a non-transitory storage medium having stored thereon texture feature images generated based on the acquired medical images;
    a computer system configured to:
        communicate with the communications connection to receive the medical images;
        communicate with the non-transitory storage medium to access the texture feature images;
        determine, using the medical images and the texture feature images, a plurality of segmentation surfaces by iteratively adjusting a relationship between a region growing algorithm that selects a region of interest (ROI) to determine a given segmentation surface and cost function for evaluating the given segmentation surface; and
        generate a report using the plurality of segmentation surfaces indicating at least boundaries between anatomical structures with functional differences in the medical images.

12. The system of claim 11 wherein the computer system is further configured to synthesize the plurality of segmentation surfaces into a segmentation report.

13. The system of claim 12 wherein the computer system is further configured to calculate a probabilistic estimate of a probabilistic segmentation surface from the plurality of segmentation surfaces when synthesizing the plurality of segmentation surfaces into a segmentation report.

14. The system of claim 12 wherein the computer system is further configured to use information from the segmentation report to program operation of a radiation therapy system for a delivery of radiation therapy to the subject.

15. The system of claim 12 wherein the computer system is further configured to perform an expectation maximization algorithm when the synthesizing the plurality of segmentation surfaces into a segmentation report.

16. The system of claim 15 wherein the expectation maximization algorithm includes a simultaneous truth and performance level estimation (STAPLE) algorithm.

17. The system of claim 11 wherein the relationship between the region growing algorithm and the cost function is defined by a single variable.

18. The system of claim 17 wherein the single variable is an inhomogeneity parameter that is used by the region growing algorithm to determine a largest segmentation surface that yield a degree of inhomogeneity less than a maximum acceptable measure of inhomogeneity and is used by the cost function to evaluate the largest segmentation surface to control inter-voxel and intra-voxel variances relative to the largest segmentation surface.

19. The system of claim 17 wherein the single variable is disregarded when generating the report.

20. The system of claim 17 wherein the computer system is configured to use the single variable as a stopping criteria when determining the plurality of segmentation surfaces.

* * * * *